United States Patent [19]

Heffernan et al.

[11] Patent Number: 4,760,155

[45] Date of Patent: Jul. 26, 1988

[54] PLATINUM CO-ORDINATION COMPOUNDS

[76] Inventors: James G. Heffernan, 113 Kennedy Dr., Pangbourne, Berks, RG87LD; Paul C. Hydes, 13 Woodlands Grove, Caversham, Reading, Berks, RG4 ONB, both of England; Donald H. Picker, 310 Woodside Ave., Narbert, Pa. 19380

[21] Appl. No.: 873,130

[22] Filed: Jun. 11, 1986

Related U.S. Application Data

[63] Continuation-in-part of Ser. No. 625,251, Jun. 27, 1984, abandoned.

[30] Foreign Application Priority Data

Jun. 11, 1985 [EP] European Pat. Off. ........ 85304131.7

[51] Int. Cl.$^4$ ............................................. C07F 15/00
[52] U.S. Cl. .................................... 556/136; 556/137; 514/492
[58] Field of Search ............................... 556/136–137; 514/492

[56] References Cited

U.S. PATENT DOCUMENTS

| | | | |
|---|---|---|---|
| 4,372,890 | 2/1983 | Yoshikumi et al. | 556/137 |
| 4,500,465 | 2/1985 | Amundsen | 556/137 |
| 4,560,781 | 12/1985 | Totani et al. | 556/137 |
| 4,577,038 | 3/1986 | Totani et al. | 556/137 |
| 4,607,114 | 8/1986 | Nakayama | 556/137 |

FOREIGN PATENT DOCUMENTS

0099133 1/1984 European Pat. Off. .

OTHER PUBLICATIONS

Organometallic and Coordination Chemistry of Platinum, 1974 ed., Academic Press, Belluco.

*Primary Examiner*—John Kight
*Assistant Examiner*—Garnette D. Draper
*Attorney, Agent, or Firm*—Cushman, Darby & Cushman

[57] ABSTRACT

Platinum co-ordination compounds comprising at least one amine ligand and a functional group remotely bonded to the amine ligand, which functional group may be linkable to a monoclonal antibody to provide a moiety which stabilizes the antibody against in vivo hydrolysis.

5 Claims, No Drawings

PLATINUM CO-ORDINATION COMPOUNDS

This is a continuation-in-part of application Ser. No. 625,251, filed June 27, 1984 which was now abandoned upon the filing hereof.

This invention relates to novel platinum co-ordination compounds for the treatment of cancer and which may be linkable to monoclonal antibodies. It also provides complexes comprising novel platinum co-ordination complexes and monoclonal antibodies, for use as site-specific or disease-specific chemotherapeutic agents.

The use of platinum co-ordination compounds, especially cisplatin (cis-diamine-dichloroplatinum II) and certain analogues thereof, in the chemotherapeutic treatment of cancer is now an established clinical technique, although efforts persist to find improved compounds. The problems with such compounds when administered as a composition together with an inert carrier or diluent is that they are absorbed generally into the systemic circulation from where they have a toxic effect on normal cells and tissues as well as on the diseased cells and tissues which they are designed to treat. In practice, the maximum dose that can be administered is limited not by pharmaceutical effectiveness but by toxicity, with the result that the patient suffers unpleasant or even severe side-effects.

In an attempt to render platinum compounds specific for certain types of tumour cell, European patent specification 0099133 proposes platinum complexed anti-tumour immunoglobulins prepared by reacting platinum salts, particularly $K_2PtCl_4$, with anti-tumour reactive immunoglobulins in for example phosphate buffered saline. The toxicity of the resulting complex is said to be lower than that of cisplatin. However, despite the presence of the immunoglobulin (which is an antibody produced from a tumour-associated antigen), the complexes are believed to be relatively non-specific in practical usage because of poorly defined metal stoichiometry and because they are hydrolysed in vivo before they reach the target tumour site, thereby losing their activity.

It has also been proposed in general pharmacological terms to link known chemotherapeutic agents to monoclonal antibodies for the purposes of rendering the agent site- or disease-specific but again the problem of in vivo stability remains.

It is an object of the present invention to provide co-ordination compounds of platinum which inter alia may be chemically linkable to monoclonal antibodies in such a way that the desired in vivo stability is obtained. It is a further object of the invention to provide conjugate platinum co-ordination compound/monoclonal antibody complexes for localised pharmacological activity and which are stable in vivo until they reach the target site.

We have found that platinum co-ordination compounds can be linked to monoclonal antibodies in such a way that the desired in vivo stability is achieved by providing the compounds with a linkable functional group remotely bonded to an amine group, the functional group forming part of an antibody-stabilising moiety.

Accordingly, the present invention provides a co-ordination compound of platinum including as ligand therein at least one amine group, wherein the compound includes a functional group remotely bonded to the said amine group.

Compounds according to the invention may be per se pharmacologically active and/or linkable to monoclonal antibodies via the said functional group.

Preferably, compounds according to the invention have the general formula

in which the X groups are the same or different and comprise either monodentate ligands selected from the class consisting of halogen, pseudohalogen, sulphate, phosphate, nitrate, carboxylate and water, or together comprise a bidentate ligand selected from the class consisting of malonate, cycloalkanedicarboxylate and cycloalkenedicarboxylate ligands, R is selected from the class consisting of hydrogen, lower (for example containing up to four carbons) alkyl, aryl, aralkyl, alkenyl, cycloalkyl and cycloalkenyl, R' is selected from lower alkyl, aryl, alkaryl, aralkyl, alkenyl, cycloalkyl and cycloalkenyl residues, or R and R' together are selected from the class consisting of methylene or polymethylene, cycloalkyl, cycloalkenyl and aryl residues, R" is hydrogen, methylene or polymethylene, and Y is a functionalising group.

The functionalising group Y may be selected from carboxylic acid and derivatives thereof, for example esters, ethers, alcohol, thiol, amine, amide, sulphonamide, nitro and halo group or may form an ether linkage with adjacent R' and R" groups when these groups comprise methylene groups.

Where R' represents a polymethylene group (i.e. an alkyl residue), it may optionally include ether, ester and/or peptide groups.

The carboxylate, malonate, cycloalkanedicarboxylate, cycloalkenedicarboxylate, and the R and R' groups in the above formula may be substituted or unsubstituted. Substituent groups may include lower (for example up to four carbons) alkyl, aryl, aralkyl, alkenyl, cycloalkyl, cycloalkenyl, alkoxy or hydroxy groups.

The amine ligands of known platinum co-ordination compounds are generally more strongly bound to the platinum than are the anionic ligands (X in the above formula). Consequently, there is no particular need chemically to provide enhanced stability of the functional group although such enhanced stability may optionally be provided when the R and R' groups together represent a chelating polymethylene, cycloalkyl, cycloalkenyl or aryl residue, whereby a cyclic (preferably 5- or 6-membered) system is formed.

The polymethylene group of a functionalised polymethylene moiety, which may optionally contain ether, ester and/or peptide groups, may have a total carbon chain length of $C_2$ to $C_{20}$, preferably $C_2$ to $C_{15}$. Examples of functionalised polymethylene moieties including ester groups are short- and medium-chain polymethylene mono-esters of dibasic carboxylic acids such as succinnic acid; examples of the inclusion of ether groups are glycols.

Particular exemplary functionalised polymethylene moieties optionally including ether and/or ester groups include the following:

—(CH$_2$)$_2$CO$_2$H
—(CH$_2$)$_4$CO$_2$H
—(CH$_2$)$_5$CO$_2$H
—(CH$_2$)$_6$OH
—(CH$_2$)$_{10}$CO$_2$H
—(CH$_2$)$_{11}$OH
—(CH$_2$)$_2$NH$_2$
—(CH$_2$CH$_2$O)$_3$H
—OCO(CH$_2$)$_2$CO$_2$H
—(CH$_2$)$_6$OCO(CH$_2$)$_2$CO$_2$H and
—(CH$_2$)$_{11}$OCO(CH$_2$)$_2$CO$_2$H On the anionic ligand side of the compound, we prefer that the X groups together comprise a bidentate malonate or cycloalkanedicarboxylate, which may be substituted or unsubstituted, or are the same monodentate halogen, preferably chlorine.

The invention also includes compounds of formula (I) modified by the addition of trans-bis-hydroxy or bis-halo groups.

Examples of compounds according to the invention include the following (where Y has the same meaning as in the general formula, for example any of the functionalising groups in the above list):

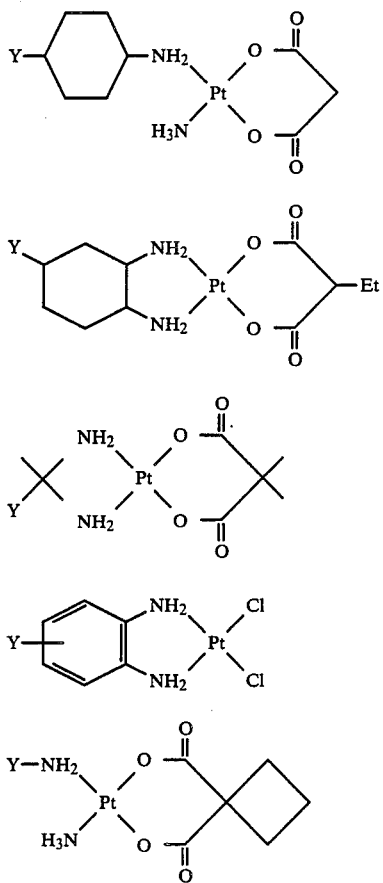

Particular compounds according to the invention include the following:

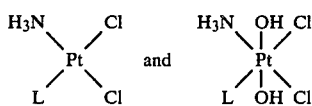

-continued

where L is

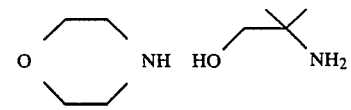

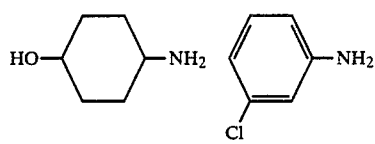

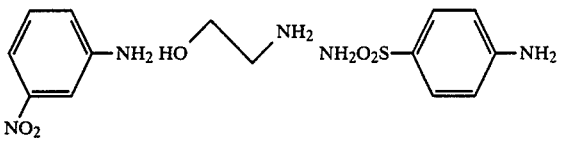

Compounds according to the invention may be linkable to monoclonal antibodies. The invention accordingly also includes a conjugate amine-containing platinum co-ordination compound/monoclonal antibody complex in which the monoclonal antibody is linked to the platinum compound via a functional group which is remotely bonded to the said amine group and which forms part of an in vivo antibody-stabilising moiety.

Conjugate complexes according to the invention have the general formula $$[(M-Z-R'NH_2)(RNH_2)PtX_2] \quad \text{(II)}$$

in which R, R' and X have the meanings defined above, Z is a functionalised polymethylene moiety in which the functionalising group is selected from —CO$_2$—, —O— or —NH—, and M is a monoclonal antibody. The functionalised polymethylene moiety may optionally include ether, ester and/or peptide groups.

Preferably the —Z—M moiety in the above formula comprises a peptide linkage although dioxide bridge linkages are possible.

The invention also includes a pharmaceutical composition for the treatment of cancer and comprising an effective amount of a compound of formula (I) or formula (II) in association with a pharmaceutically-acceptable carrier, diluent or excipient. Such compositions may be suitable for oral or parenteral administration, and may be in unit dosage form.

The preparation of compounds according to the invention will now be described by way of example.

EXAMPLE 1

Dichloroamine(4-amino-ethylbutyrate)platinum-(II)[PtCl$_2$NH$_3$(NH$_2$(CH$_2$)$_3$CO$_2$Et)]

To a solution of K[PtCl$_3$(NH$_3$)] (4.0 g, 11.2 mmol) in water (20 ml) a solution of 4-amino-ethylbutyrate.HCl (2.0 g, 11.9 mmol) and potassium carbonate (1.2 g, 8.7 mmol) in water (10 ml) was added. The reaction mixture was stirred for 1.5 hrs during which time a green-yellow solid precipitated. This solid was collected, dissolved in a minimal volume of dimethylactamide (DMA) and re-precipitated with 2-propanol. The pale green-yellow product was collected, washed with ethanol and ether and dried in vacuo. Yield=0.35 g, 7% based on Pt.

| | | C | H | N | Cl |
|---|---|---|---|---|---|
| Analysis: | % Calc. | 17.40 | 3.88 | 6.78 | 17.12 |
| | % Found | 17.67 | 3.89 | 6.59 | 17.62 |

Ir(KBr): 3260(m), 3220(m)cm$^{-1}$ ($v_{N\text{-}H}$) 1715(s)cm$^{-1}$ ($v_{CO}$) 2970(m)cm$^{-1}$ ($v_{C\text{-}H}$) 320(m), 330(sh)cm$^{-1}$ ($v_{Pt\text{-}Cl}$)

EXAMPLE 2

Dichloroammine(p-aminobenzoic acid)platinum(II)[PtCl$_2$NH$_3$(NH$_2$C$_6$H$_4$CO$_2$H)]

To a solution of K[PtCL$_3$(NH$_3$)] (6.2 g, 17.4 mmol) in water (30 ml) was added a solution of p-aminobenzoic acid (2.4 g, 17.5 mmol) and sodium bicarbonate (1.5 g, 17.9 mmol) in 40 ml of water. N$_2$ was bubbled through the solution and the reaction mixture was stirred for 1 hr. 2N HCl (50 ml) was then added, precipitating a light brown solid. This material was collected, washed with ethanol and dried in vacuo. Yield=1.9 g. The complex was purified by dissolving the crude product in 5 ml DMA/acetone (4:1 V/V). Ether was added to this solution to form an oil. Trituration of the oil with acetone yielded a tan solid which was collected, washed with acetone and ether and dried in in vacuo. Yield=0.5 g, 7% based on Pt.

| | | C | H | N | Cl |
|---|---|---|---|---|---|
| Analysis: | % Calc. | 20.01 | 2.40 | 6.67 | 16.87 |
| | % Found | 20.45 | 2.46 | 6.59 | 16.81 |

Ir (KBr): 3500(b)cm$^{-1}$ ($v_{O\text{-}H}$) 3280(m), 3235(m), 3210(m), 3130(m)cm$^{-1}$ ($v_{N\text{-}H}$) 1685(s)cm$^{-1}$ ($v_{CO}$) 325(m), 335(sh)cm$^{-1}$ ($v_{Pt\text{-}Cl}$)

EXAMPLE 3

Cis-Amminedichloromorpholineplatinum(II)

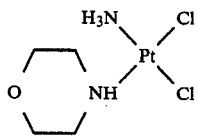

K$_2$[PtCl$_4$] (40 mmol, 16.75 g) was dissolved in water (150 ml), filtered and potassium iodide (160 mmol, 26.72 g) in water (25 ml) added to the stirred filtrate, followed immediately by morpholine (88 mmol, 7.67 g). Stirring was continued for 2 h. The yellow precipitate was filtered off, washed with water and then ethanol and dried in air to give cis-diiodimorphlineplatinum(II) (24.152 g, 98%).

Cis-[PtI$_2$(morpholine)$_2$] (24.52 g, 39.36 mmol) was suspended in acetone (300 ml) and aqueous HClO$_4$ (160 mmol, 2.86M solution, 56 ml) added and the mixture stirred for 4 h. The resulting red solid was filtered off, washed with acetone (20 ml) and dried in air to give oligomeric diidomorpholineplatinum(II) (18.2 g, 86%.

[PtI$_2$(morpholine)]$_n$ (18.2 g, 33.96 mmol Pt) was stirred with water (100 ml) and aqueous ammonia (1M, 2.5×excess, 84.9 ml) added. Stirring was continued overnight and the yellow solid filtered off, washed with water and dried in vacuo to give cis-amminediiodomorpholineplatinum(II) (17.29 g, 92%).

Cis-[PtI$_2$(NH$_3$)(morpholine)] (17 g, 30.74 mmol) was added portionwise to a stirred solution of AgNO$_3$ (1.95 eq., 59.94 mmol, 10.19 g) in water (50 μl). The suspension was stirred for 2 h in the absence of light, charcoal (ca. 0.2 g) added and stirring continued for a further 5 minutes. The silver iodide was then removed by filtration and the filter cake washed once with water (20 ml). The combined filtrates gave a negative test for Ag$^+$ and were then added to concentrated HCl (10 ml) and stirred for 2 h. The resulting yellow solid was filtered off, washed well with water and dried in vacuo to give cis-amminedichloromorpholineplatinum(II), found: C 13.02, H 3.10, N 7.62, Cl 18.95%, C$_4$H$_{12}$N$_2$OCl$_2$Pt requires C 12.97, H 3.24, N 7.57, Cl 19.19%.

EXAMPLE 4

Amminedichlorodihydroxymorpholineplatinum(IV)-perhydrate

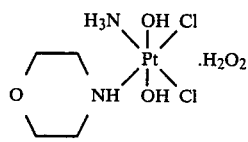

[PtCl$_2$(NH$_3$)(morpholine)] (4.24 g, 11.46 mmol) was suspended in 30% H$_2$O$_2$ (20 ml) and stirred at 60°–70° for 3 h, with further H$_2$O$_2$ (10 ml) added after 2 h. The yellow solution was allowed to cool overnight and then cooled in an ice bath. The resulting yellow crystals were collected and washed with water to give amminedichlorodihydroxymorpholineplatinum(IV) (2.37 g, 51%). Microanalysis indicated a perhydrate: found C 10.88, H 3.60, N 6.31, Cl 16.79%, C$_4$H$_{14}$N$_2$O$_3$Cl$_2$Pt.H$_2$O$_2$ requires C 10.95 H 3.65 N 6.39, Cl 16.2%.

EXAMPLE 5 cis-(2-Amino-2-methyl-1-propanolamminedichloroplatinum(II)

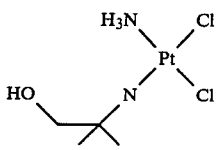

Potassium iodide (9.63 g, 58 mmol) in water (10 ml) was added to a stirred solution of K[PtCl$_3$(NH$_3$)] (6.8 g, 19 mmol) in water (60 ml) followed immediately by 2-amino-2-methyl-1-propanol (1.78 g, 20 mmol). The mixture was stirred for 1 h, filtered and the yellow solid washed well with water and dried in vacuo to give cis-ammine(2-amino-2-methyl-1-propanol)diiodoplatinum(II) (5.1 g, 48%).

This diiodide (5.0 g, 9.01 mmol) was added in portions of a stirred solution of silver nitrate (1.95 eq., 2.984 g, 17.57 mmol) in water (50 ml). Stirring was continued for 2 h in the dark, charcoal (0.2 g added) and stirring continued for 5 min. The silver iodide was filtered off, washed once with water (ca. 10 ml) and the combined filtrates tested for free Ag$^+$. No silver was detected so concentrated HCl (10 ml) was added to the stirred solution, and stirring continued for 1 h. The pale yellow solid was collected by filtration, washed with water and dried in vacuo to give cis-(2-amino-2-methyl-1-propanol)amminedichloroplatinum(II) (3.05 g, 91%), found: C 12.68, H 3.79, N 7.51, Cl 19.08%, $C_4H_{14}N_2OCl_2Pt$ requires: C 12.90; H, 3.76, N 7.53, Cl 19.09%.

EXAMPLE 6

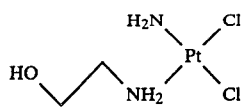

Potassium iodide (9.46 g, 57 mmol) in the minimum quantity of water (ca. 10 ml) was added to a stirred solution of $K[PtCl_3(NH_3)]$ followed immediately by ethanolamine (1.22 g, 20 mmol). A yellow precipitate formed within 5 minutes, after which the mixture was cooled in an ice-bath and stirring continued for 1 h. The solid was filtered off, washed with ice-cold water (2×10 ml) and dried in air to give cis-amminediiodo(ethanolamine)platinum(II) (6.07 g, 61%).

The diiodide (6.07 g, 11.52 mmol) was added in portions to a solution of $AgNO_3$ (3.874 g, 22.81 mmol, 1.98 eq.) in water (15 ml) and stirred for 2 h in the dark. Charcoal (ca. 0.2 g) was then added, stirring continued for 5 min, the silver iodide filtered off, washed once with water (ca. 10 ml) and the combined filtrates tested for $Ag^+$. No silver was detected and so concentrated HCl (5 ml) was added and the solution stirred 5 min at room temperature and then at 0° for 1 h. The bright yellow solid was filtered off, washed carefully with ice-cold water and dried in vacuo to give cis-amminedichloro(ethanolamine)platinum(II) (3.8 g, 96%); found: C 6.72, H 2.77, N 7.85, Cl 20.61%, $C_2H_{10}N_2OCl_2Pt$ requires: C 6.98, H 2.93, N 8.14, Cl 20.60%.

EXAMPLE 7 cis-Amminedichloro(4-hydrocyclohexylamine)-platinum(II)

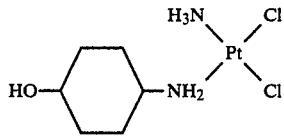

Potassium iodide (12.5 g, 75 mmol) in water (20 ml) was added to a stirred solution of $K[PtCl_3(NH_3)]$ (9.0 g, 25 mmol) in water (60 ml) followed immediately by 4-hydroxycyclohexylamine (3.0 g, 26.3 mmol). The mixture was stirred for 1 h and cooled for the last 15 min in ice to promote crystallisation. The grey-yellow solid was filtered off, washed with ice-cold water, ethanol (red coloured washings) and ether and dried in vacuo to give cis-amminediiodo(4-hydroxycyclohexylamine)platinum(II) (5.9 g, 41%).

The diiodo compound (5.9 g, 10.2 mmol) was added in portions to a stirred solution of silver nitrate (3.41 g, 20 mmol) in water (17 ml). The mixture was stirred in the dark for 2 h, charcoal (ca. 0.2 g) added and stirring continued a further 5 min. The silver iodide was removed by filtration, washed once with water (ca. 10 ml) and the combined filtrates tested for free $Ag^+$. No silver was detected and so concentrated HCl (5 ml) was added to the filtrate and stirred for ½ h, then cooled in ice and the pale yellow solid filtered off, washed with ice-cold water, ethanol and ether and dried to vacuo to give cis-amminedichloro(4-hydroxycyclohexylamine)-platinum(II) (3.0 g, 75%), found: C 17.62, H 3.95, N 6.98, Cl 17.62%; $C_6H_{16}N_2OCl_2Pt$ requires: C 18.09, H 4.05, N 7.04, Cl 17.80%.

EXAMPLE 8 cis-Amminedichloro(3-chloroaniline)platinum(II)

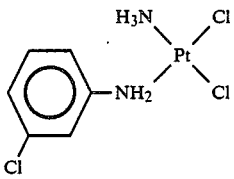

Potassium iodide (9.7 g, 58 mmol) in water (20 ml) was added to a stirred solution of $K[PtCl_3(NH_3)]$ (6.97 g, 19.5 mmol) in water (60 ml) followed immediately by 3-chloroaniline (2.55 g, 20 mmol). Ethanol (ca. 1 ml) was then added and stirring continued for 1 h. The resulting yellow/brown solid was filtered off, washed with water and then ethanol and dried in vacuo to give cis-ammine(3-chloroaniline)diiodoplatinum(II) (6.9 g, 59%).

The diiodide (6.8 g, 11.5 mmol) was added in portions to a stirred solution of silver nitrate (3.725 g, 21.85 mmol, 1.9 eq.) in water (20 ml). Stirring was continued for 2 h in the dark, charcoal (ca, 0.2 g) added, stirring continued a further 5 min and the silver iodide removed by filtration, washed once with water (ca. 10 ml) and the combined filtrates tested for $Ag^+$. No silver was detected so concentrated HCl (18 ml) was added and stirred for 45 min. The resulting cream coloured solid was filtered off, washed with water and then ethanol and dried in vacuo to give cis-amminedichloro(3-chloroaniline)platinum(II) (2.6 g, 55%), found: C 17.40, H 1.95, N 6.80, Cl 25.48%; $C_6H_{10}N_2Pt$ requires: C 17.55, H 2.21, N 6.82, Cl 25.90%.

EXAMPLE 9 cis-(5-Amino-1-pentanol)amminedichloroplatinum(II)

Potassium iodide (9.46 g, 57 mmol) in water (10 ml) was added to a stirred solution of $K[PtCl_3(NH_3)]$ (6.8 g, 19 mmol) in water (60 ml) followed immediately by 5-amino-1-pentanol (2.06 g, 20 mmol). The solution was stirred for 102 h then cooled in ice and the resulting pale orange solid filtered off, washed with water and then ethanol and dried in air to give cis-(5-amino-1-pentanol)amminediiodoplatinum(II) (8.72 g, 80.7%).

The diiodide (8.62 g, 15.15 mmol) was added in portions to a stirred solution of $AgNO_3$ (5.096 g, 30 mmol, 1.98 eq.) in water (20 ml). Stirring was continued in the dark for 2 h, charcoal (ca. 0.2 g added) and stirring continued a further 5 min. Concentrated nitric acid (5 ml) was added, the solution filtered through a bed of celite and finally through two layers of Whatman 542 paper to give a clear, yellow filtrate with no free silver present. Concentrated HCl (5 ml) was added and the mixture stirred for 1 h. The pale green solid was filtered off, washed with water, ethanol and ether and dried to give cis-(5-amino-1-pentanol)amminedichloroplatinum-(II) (2.7 g, 45%).

EXAMPLE 10 cis-Amminedichloro(3-nitroaniline)platinum(II)

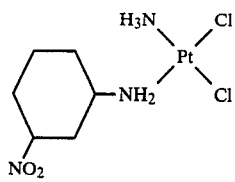

K[PtCl₃(NH₃)] (7.15 g, 20 mmol) in water (50 ml), KBr (7.14 g, 60 mmol) in water (20 ml) and 3-nitroaniline (2.76 g, 20 mmol) in dichloromethane (75 ml) were mixed together, tetra-n-butylammonium chloride (0.1 g) added and the reaction stirred for 2 h at room temperature. The yellow solid was filtered off, washed with water and then ethanol and dried in air to give cis-amminedibromo(3-nitroaniline)platinum(II) (7.55 g, 74%).

The dibromide (7.35 g, 14.4 mmol) was added in portions to a stirred solution of AgNO₃ (4.774 g, 28.1 mmol, 1.95 eq.). Stirring was continued for 2 h in the dark, charcoal (ca. 0.2 g) added. Stirring continued for 5 min, the silver bromide filtered off, washed once with water (ca. 10 ml) and the combined filtrates tested for Ag⁺. No silver was detected and so concentrated HCl (10 ml) was added and stirred for 1 h. The pale yellow solid was filtered off, washed with water and then ethanol and dried in vacuo to give cis-amminedichloro(3-nitroaniline)platinum(II) (5.7 g, 94%); found: C 16.82, H 1.98, N 9.81, Cl 16.41%; C₆H₉N₃Cl₂Pt requires C 17.10, H 2.14, N 9.98, Cl 16.86%.

EXAMPLE 11 cis-amminedichloro(sulphanilamide)platinum(II)

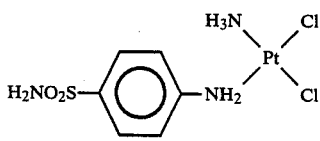

Sulphanilamide (3.44 g, 20 mmol) was dissolved in ethyl acetate (500 ml) and solutions of K[PtCl₃(NH₃)] (7.15 g, 20 mmol) in water (50 ml) and potassium bromide (7.14 g, 60 mmol) in water (25 ml) added, followed by solid tetrabutylammonium chloride. The mixture was vigorously stirred for 6 h. The yellow solid was collected by filtration and washed with water and then ethanol and dried to give cis-amminedibromo(sulphanilamide)platinum(II) (6.95 g, 64%).

The dibromide (6.8 g, 12.5 mmol) was added in portions to a solution of AgNO₃ (4.141 g, 24.375 mmol, 1.95 eq.) in water (50 ml) and acetone 20 ml). Stirring was continued for 2 h in the dark. Charcoal (ca. 0.2 g) was then added, stirring continued for 5 min and the silver iodide filtered off, washed once with water (ca. 10 ml) and the combined filtrates tested for Ag⁺. No silver was detected so concentrated HCl (10 ml) was added and stirred for 2 h. The pale yellow solid was filtered off, washed well with water and dried to give cis-amminedichloro(sulphanilamide)platinum(II) (4.37 g, 77%) found: C 15.56, H 2.41, N 9.21, Cl 15.20%; C₆H₁₁N₃SO₂Cl₂Pt requires: C 15.82, H 2.42, N 9.23, Cl 15.60%.

Also prepared in similar fashion were dichloroammine (glycylglycine ethyl ester)platinum(II) (Elemental analysis found C 16.14%, H 3.29%, N 9.41%, Cl 15.94%: formula requires C 16.26%, H 3.42%, N 9.48%, Cl 15.99%). Dichloroammine(glycylglycine)-platinum(II) (Elemental analysis found C 10.91%, H 2.86%, N 8.60%, Cl 17.56%: formula requires C 11.57%, H 2.68%, N 10.12%, Cl 17.08%).

Cis trans-dichlorodihydroxyethylenediamine carboxylatoplatinum(IV) (Elemental analysis found C 8.51%, H 2.86%, N 6.51%, Cl 16.69%: formula requires C 8.53%, H 2.86%, N 6.64%, Cl 16.79%). (2,3 diamino propionic acid)platinum(II)malonate (Elemental analysis found C 20.32%, H 2.90%, N 6.75% formula requires C 20.24%, H 2.92%, N 6.75%).

Conjugate platinum coordination compound/monoclonal antibody complexes according to the invention may be prepared for example according to the following scheme, in which the functionalising group is —CO₂H:

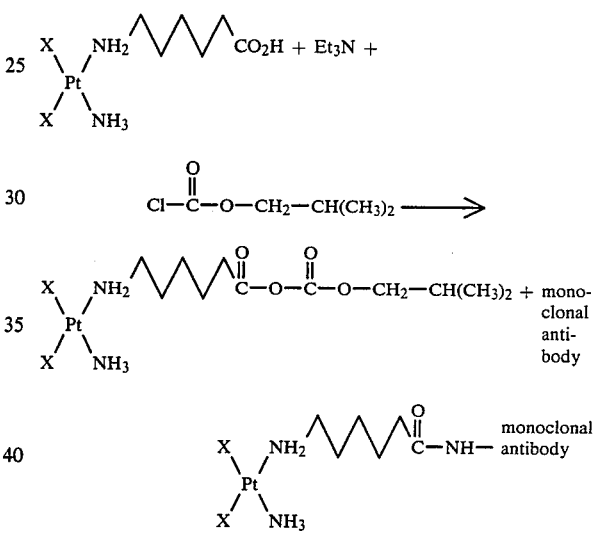

According to the above scheme, the antibody is linked to the platinum compound via a peptide group. Once at the desired site, enzymes which are present in tumour cells are able to catalyse hydrolysis thereby releasing the active anti-tumour moiety. Similarly, other functional groups may be linked to antibodies using conventional synthetic routes.

EXAMPLE 12

This example describes a method for linking the platinum complex to a monoclonal antibody which is suitable for use when the functional group is a carboxylic acid moiety.

The platinum complex is dissolved in a minimum of distilled water and brought to a pH of about 8 by the addition of 1N NaOH. The solution is then added to a monoclonal antibody at a concentration of 10 mg ml⁻¹. 1-Ethyl-3-(3-dimethylaminopropyl)carbodiimidehydrochloride (20 fold excess) is next added and the reaction stirred in the dark for 18 h at 25° C. The reaction is quenched by the addition of sodium acetate-acetic acid buffer (pH 4.7), then dialysed against distilled water and passed through a gel filtration medium to obtain monoclonal antibodies linked to platinum.

Anti-tumour testing results

Compounds according to the invention were tested against ADJ/PC6 tumour in Balb/C mice to determine the figures for $LD_{50}$, $ED_{90}$ and TI (therapeutic index: $LD_{50}/ED_{90}$). Administration was either intraperitoneal (I.P.) or per os (P.O.).

Results are as follows:

| COMPOUND | ROUTE OF ADMIN | $LD_{50}$ | $ED_{90}$ | TI |
|---|---|---|---|---|
| H₃N\\Pt/Cl / C₂H₅O₂(CH₂)₃NH₂ \\Cl | I.P. | 35 | 0.65 | 53.8 |
|  | P.O. | 265 | 35 | 4.7 |
| H₃N\\Pt/Cl / HO-C₆H₄-NH₂ \\Cl | P.O. | 119 | 47 | 2.5 |

We claim:

1. A co-ordination compound of platinum having the general formula

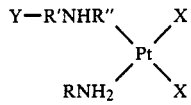

in which the X groups are either the same or different and comprise monodentate ligands selected from the class consisting of halogen, pseudohalogen, sulphate, phosphate, nitrate, carboxylate and water, or together comprise a bidentate ligand selected from the class consisting of malonate, cycloalkanedicarboxylate and cycloalkenedicarboxylate ligands, R is selected from the class consisting of hydrogen, lower alkyl, aryl, aralkyl, alkenyl, cycloalkyl and cycloalkenyl, R' is selected from lower alkyl, aryl, alkaryl, aralkyl, alkenyl, cycloalkyl and cycloalkenyl residues, or R and R' together are selected from the class consisting of a methylene or polymethylene, cycloalkyl, cycloalkenyl or aryl residues, R" is hydrogen, methylene or polymethylene, and Y is a functionalising group selected from carboxylic acid and derivatives thereof, ethers, alcohol, thiol, amine, amide, sulphonamide, nitro and halo or forms an ether linkage with adjacent R' and R" groups when the R' and R" groups comprise methylene groups.

2. A compound according to claim 1 in which R' represents a polymethylene group which includes ether or ester groups.

3. A compound according to claim 1 modified by the addition of trans-bis hydroxy or -bis halo groups.

4. A pharmaceutical composition for the treatment of cancer comprising an effective amount of a compound according to claim 1 in association with a pharmaceutically-acceptable carrier, diluent or excipient.

5. A composition according to claim 4 in unit dosage form.

* * * * *